US00PP22450P3

(12) United States Plant Patent

Karniel et al.

(10) Patent No.: US PP22,450 P3

(45) Date of Patent: Jan. 10, 2012

(54) GRAPE PLANT NAMED 'ARRAFOURTEENONE'

(50) Latin Name: *Vitis vinifera*
Varietal Denomination: ARRAFOURTEENONE

(75) Inventors: Shachar Karniel, Edison, CA (US); Sal Giumarra, Edison, CA (US)

(73) Assignee: Agricultural Research and Development Limited Liability Company, Edison, CA (US)

( * ) Notice: Subject to any disclaimer, the term of this patent is extended or adjusted under 35 U.S.C. 154(b) by 0 days.

(21) Appl. No.: 12/660,721

(22) Filed: Mar. 2, 2010

(65) Prior Publication Data

US 2011/0219500 P1 Sep. 8, 2011

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

| | | | |
|---|---|---|---|
| PP16,399 | P3 | 4/2006 | Ellis et al. |
| PP17,223 | P3 | 11/2006 | Giumarra et al. |
| PP17,224 | P3 | 11/2006 | Giumarra et al. |
| PP18,625 | P3 | 3/2008 | Pinhas et al. |

*Primary Examiner* — Susan McCormick Ewoldt

(74) *Attorney, Agent, or Firm* — Christie, Parker & Hale, LLP

(57) ABSTRACT

A new distinct variety of grapevine named ARRAFOURTEENONE abundantly forms attractive large seedless berries having a purple red skin coloration in large clusters. The fruit displays a natural flavor and is firm in texture. The fruit commonly is ready for harvesting during the end of July in San Joaquin Valley of Central California, U.S.A., and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRAFOURTEENONE'.

BACKGROUND OF THE INVENTION

A breeding program was initiated during the late 90's near Bakersfield in San Joaquin Valley of Central California. In 2004, during this breeding program, a new variety of *Vitis vinifera* was created by deliberate cross breeding of two parent plants by emasculation of the pollen bearing organ of the male and introducing pollen from another male origin. The female parent of the new variety was the GZR1 seedless grape variety (non-patented in the United States). The male parent (i.e. the pollen parent) of the new variety was GAR5 (non-patented in the United States).

Comparison between ARRAFOURTEENONE and Autumn Royal

| | ARRAFOURTEENONE | AUTUMN ROYAL |
|---|---|---|
| Harvest Time | Mid Early | Late |
| Shape | Ovoid | Narrow Ellipsoid |
| Vigor | Medium vigor | Weak vigor |
| Berry shape | Broad ellipsoid | Cylindrical |

The parentage of the new variety can be summarized as follows:

GZR1×GAR5.

An artificial pollination was created, and the result was an embryo which possessed unique genetic qualities. The rudiments resulting from the above pollination were embryo rescued.

The plant was then transplanted to Bakersfield in San Joaquin Valley of Central California.

It was found that the new grapevine of the present invention possesses the following combination of characteristics:

(a) Forms attractive large seedless berries having purple red skin coloration in large clusters which display a natural flavor;

(b) Commonly bears fruit during the end of July in the San Joaquin Valley of Central California, U.S.A.; and (c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2007 near Bakersfield in the San Joaquin Valley of Central California, U.S.A. by grafting on mature 'Thompson Seedless' rootstock (non-patented in the United States). Such asexual propagation has been conducted thereafter in successive years through 2009, and has shown that the characteristics of the new variety are strictly transmissible from one generation to another. Accordingly, the new variety undergoes asexual propagation in a true to type manner. The age of the plant in the drawing is five years old and the variety was created in 2004.

SUMMARY OF INVENTION

The new variety ARRAFOURTEENONE is a large size, purple red seedless table grape with large production, e.g., about 40 to 50 bunches per vine, and an average of about one to two bunches per shoot.

Asexual reproduction by micro propagation of the new variety as performed near Bakersfield, Calif., U.S.A., at Arvin, Calif. Ranch 33 which shows that the forgoing and other distinguishing characteristics come true to form and are established and transmitted through succeeding propagations.

BRIEF DESCRIPTION OF THE DRAWINGS

The accompanying photographic illustration shows typical specimens of vegetative growth of five year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRAFOUR-TEENONE'.

DETAILED BOTANICAL DESCRIPTION

The chart used in the identification of colors is The R.H.S. Colour Chart of The ROYAL HORTICULTURAL SOCIETY. The description is based on the observation of plants growing on 'Thompson Seedless' rootstock outdoors near San Joaquin Valley of Central California, U.S.A.

Vine:
- *Vigor.*—Medium.
- *Productive capacity.*—Very productive.
- *Trunk.*—Slender, includes long split strips, and six years after grafting the diameter commonly is approximately 2.4 inches (approximately 62 mm) measured 1 foot above the ground and has a color of greyed-orange (174-B).

Time of bud burst:
- *Medium.*—Date of bud burst in specified location of culture is Mar. 23, 2011 season in Arvin, Calif.

Young shoot:
- *Openness of tip.*—Half open.
- *Prostrate hairs on tip.*—Medium.
- *Anthocyanin coloration of prostrate hairs on tip.*—Medium.
- *Erect hairs on tip.*—Medium.

Young leaf:
- *Color of upper side of blade.*—Green (yellow green 144-A).
- *Prostrate hairs between main veins on lower side of blade.*—Medium.
- *Erect hairs on main veins on lower side of blade.*—Medium.

Shoot:
- *Attitude (before tying).*—Semi-erect.
- *Color of dorsal side of internodes.*—Yellow-green (144-C).
- *Color of ventral side of internodes.*—Yellow-green (144-A).
- *Color of dorsal side of nodes.*—Yellow-green (144-C).
- *Color of ventral side of nodes.*—Yellow-green (144-A).
- *Erect hairs on internodes.*—Absent or very sparse.
- *Length of tendrils.*—2 tendrils 9.5 cm, 7.5 cm.

Flower:
- *Sexual organs.*—Fully developed stamens and fully developed gynoecium.

Mature leaf:
- *Size of blade.*—Very large (7.5×5 inches).
- *Shape of blade.*—Circular.
- *Blistering of upper side of blade.*—Absent or very weak.
- *Number of lobes.*—Five.
- *Depth of upper lateral sinuses.*—Absent or very shallow.

Lobed leaves:
- *Arrangement of lobes of upper lateral sinuses.*—Open.
- *Arrangement of lobes of petiole sinus.*—Slightly open.
- *Length of teeth.*—Short, 4.5 cm.
- *Ratio length/width of teeth.*—Small.
- *Shape of teeth.*—Both sides convex.
- *Proportion of main veins on upper side of blade with anthocyanin coloration.*—Medium, 4.5 cm.
- *Prostrate hairs between main veins on lower side of blade.*—Sparse.
- *Erect hairs on main veins on lower side of blade.*—Sparse.
- *Length of petiole equal compared to length of middle vein.*—Moderately shorter, petiole length is 10 cm and vein length is 12 cm.
- *Top side color.*—Yellow-green (146-A).
- *Bottom side color.*—Yellow-green (146-C).
- *Texture.*—Smooth.
- *Petiole.*—10 cm.
- *Petiole color.*—Green (146-C).
- *Petioed stripes color.*—Grayed-purple (184-D).

Reproductive organs:
- *Color.*—Green (143-A).
- *Size.*—2 mm.

Time of beginning of ripening: Medium, mid-July, Arvin, Calif. season

Bunch:
- *Size (peduncle excluded).*—Very large (12×9 inches).
- *Average weight.*—800 g.
- *Density.*—Lax, single berries, some pedicels visible.
- *Length of peduncle primary bunch.*—Long (2.5 inches).

Berry:
- *Size.*—Large, 22.2 mm.
- *Length.*—3 cm.
- *Shape.*—Obtuse ovoid.
- *Weight.*—13 g.
- *Color of skin (without bloom).*—Dark red violet (grayed purple 187-A).
- *Ease of detachment from pedicel.*—Moderately easy.
- *Thickness of skin.*—Medium, not too high and not too low.
- *Anthocyanin coloration of flesh.*—Medium.
- *Firmness and color of flesh.*—Soft or slightly firm, yellow-orange (19-D).
- *Particular flavor.*—None.
- *Formation of seeds.*—Rudimentary.
- *Market use of the observed plant.*—Fresh market.

Woody shoot:
- *Main color.*—Yellowish brown (grayed orange 184-C).

DNA profile: To further the characterize the new Arra variety DNA was extracted from dried leaf samples and DNA profiles were obtained in Spain, using base pairs for 14 standard microsatellite DNA markers. The data is presented hereafter.

| Microsatellite DNA Marker | Allele Sizes in Base Pairs | |
|---|---|---|
| MSV01 | 134 | 152 |
| MSV02 | 228 | 236 |
| MSV04 | 181 | 181 |
| MSV06 | 246 | 250 |
| MSV07 | 322 | 322 |

-continued

| Microsatellite DNA Marker | Allele Sizes in Base Pairs | |
|---|---|---|
| MSV08 | 245 | 258 |
| MSV09 | 251 | 257 |
| MSV10 | 211 | 215 |
| MSV12 | 236 | 246 |
| MSV13 | 166 | 168 |
| MSV14 | 176 | 180 |
| MSV15 | 291 | 299 |
| MSV16 | 186 | 188 |
| MSV17 | 159 | 159 |

The ARRAFOURTEENONE variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of grapevine, botanically known as *Vitis vinifera,* identified as 'ARRAFOURTEENONE', substantially as shown and described herein.

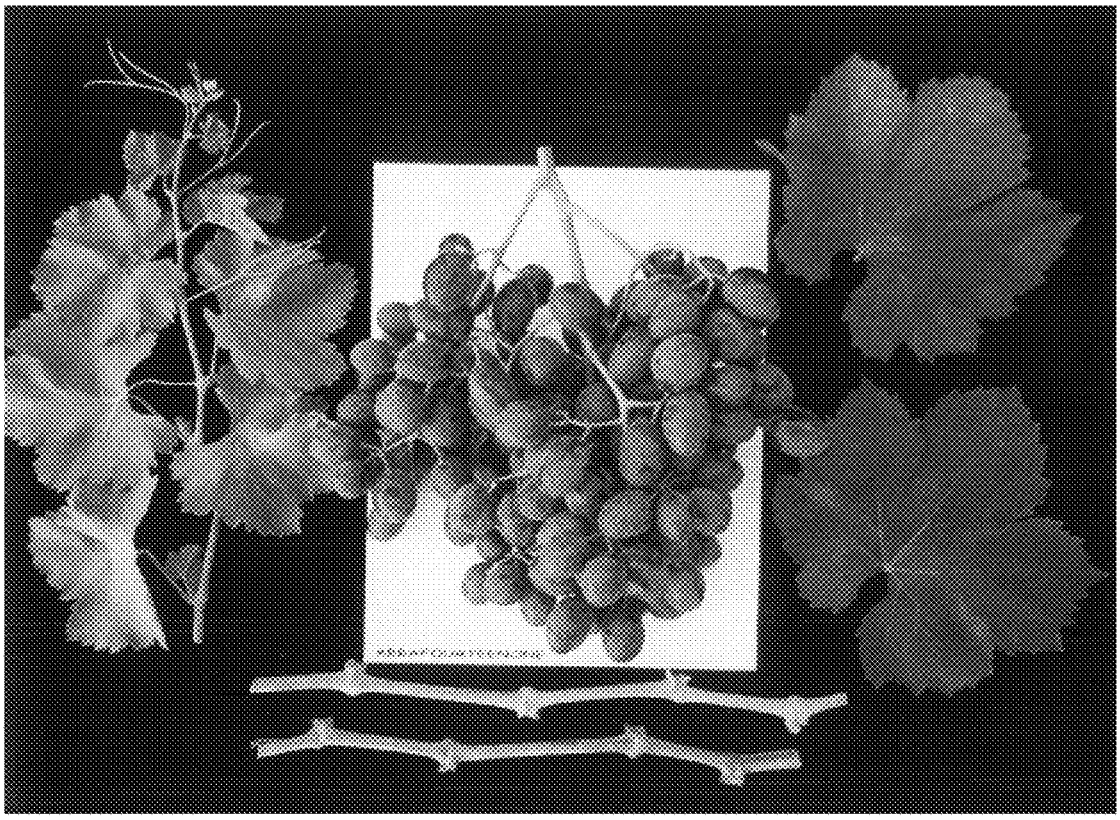

* * * * *